United States Patent [19]
Hardy et al.

[11] Patent Number: 5,143,076
[45] Date of Patent: Sep. 1, 1992

[54] THREE-DIMENSIONAL BEAM LOCALIZATION MICROSCOPE APPARATUS FOR STEREOTACTIC DIAGNOSES OR SURGERY

[75] Inventors: Tyrone L. Hardy, 806 Sagebrush Ct., SE., Albuquerque, N. Mex. 87123; Laura D. Brynildson, Albuquerque, N. Mex.

[73] Assignee: Tyrone L. Hardy, Albuquerque, N. Mex.

[21] Appl. No.: 552,164

[22] Filed: Jul. 11, 1990

Related U.S. Application Data

[60] Division of Ser. No. 428,242, Oct. 27, 1989, abandoned, which is a continuation-in-part of Ser. No. 290,316, Dec. 23, 1988, Pat. No. 5,099,846.

[51] Int. Cl.$^5$ ............................................. A61B 6/08
[52] U.S. Cl. .................................. 128/664; 606/130; 128/665
[58] Field of Search ............... 606/130, 10, 11; 128/664, 665; 350/507, 511, 515, 516, 518, 520–523, 525

[56] References Cited

U.S. PATENT DOCUMENTS

| | | | |
|---|---|---|---|
| 4,702,571 | 10/1984 | Barber | 350/516 |
| 4,813,588 | 3/1989 | Srivastara et al. | 350/523 |
| 4,832,649 | 5/1989 | Matsushita et al. | 128/665 |
| 4,905,702 | 3/1990 | Foss | 128/665 |
| 4,919,516 | 4/1990 | Peträn et al. | 350/527 |

FOREIGN PATENT DOCUMENTS

| | | | |
|---|---|---|---|
| 2384481 | 11/1978 | France | 606/130 |
| 1074239 | 12/1984 | U.S.S.R. | 350/507 |

OTHER PUBLICATIONS

"Computerized Optimization of $^{125}$I Implants in Brain Tumors" by B. Bauer-Kirpes, Ph.D. *J. Radiation Oncology Biol. Phys.*, vol. 14, pp. 1013–1023 (1987).
"External Stereotactic Irradiation by Linear Accelerator" by F. Columbo, M.D., et al. *Neurosurgery*, vol. 16, No. 2; pp. 154–159 (1985).
"The University of Florida Radiosurgery System" by W. A. Friedman, M.D. 1989, Elsevier Science Publishing Company, Inc.
"Stereotactic CT Atlases," Tyrone L. Hardy; *Modern Stereotactic Surgery*, L. D. Lunsford, Ed., Boston, pp. 425–439 (1988).
"CASS: A Program for Computer-Assisted Stereotaxic Surgery," *Proceedings of the 5th Annual Symposium on Computer Application in Medical Care*, T. L. Hardy and J. Koch; Washington, D.C., 1981, pp. 1116–1126.
"Computer-Assisted Stereotactic Surgery," Hardy, T. L. and Koch, J.; *Appl. Neurophysiol.*, vol. 45, pp. 396–398 (1982).
"Computer Graphics with Computerized Tomography for Functional Neurosurgery," Hardy, T. L., Koch, J., and Lassiter, A., *Appl. Neurophysiol.*, vol. 46, pp. 217–226 (1983).
"A Portable Computerized Tomographic Method for Tumor Biopsy," Hardy, T. L., Lassiter, A., and Koch, J., *Acta. Neurochir.*[Suppl.], (Wien) p. 444 (1983).
"Computer-Assisted Stereotactic Laser Microsurgery for the Treatment of Intracranial Neoplasms" by P. Kelly et al. *Neurosurgery*, vol. 10, No. 3, pp. 324–331 (1982).
"Computer Simulation for the Stereotactic Placement of Interstitial Radionuclide Sources onto CT-Defined Tumor Volumes," Kelly et al., *Neurosurgery*, pp. 412–444 (1984).

(List continued on next page.)

*Primary Examiner*—Peter A. Aschenbrenner
*Attorney, Agent, or Firm*—Deborah A. Peacock; Donovan F. Duggan

[57] ABSTRACT

The disclosure is directed to a method and apparatus for determining, in three dimensions, the location, size, depth and width of tumors, lesions, abnormalities, structures, and the like, particularly useful for stereotactic surgery. The invention utilizes several light beams which, when they intersect, allow for such measurements and calculations. In one embodiment, the light sources attach to a stereotactic frame. In an alternative embodiment, the light sources are incorporated within a stereotactic microscope.

7 Claims, 13 Drawing Sheets

OTHER PUBLICATIONS

"Stereotactic Surgical System Controlled by Computed Tomography" by M. Koslow, M.D., et al. *Neurosurgery*, vol. 8, pp. 72-82 (1981).

"The Ill-Conditioning in Stereotaxic Irradiation: Optimization of Isodoses Arrays Distribution Using the Singular Values Decomposition," Conference *Eighth International Conference*, Jun. 8-10, 1988.

"Exploring Design Space: Optimization as Synthesizer of Design and Analysis" by A. R. Parkinson et al. *Computers in Mechanical Engineering*, Mar. 1985, pp. 28-36.

"The Role of Computed Tomography and Digital Radiographic Techniques in Stereotactic Procedures for Electrode Implantation and Mapping, and Lesion Localization," by T. M. Peters et al., *Appl. Neurophysiol.*, vol. 46, pp. 200-205 (1983).

"Measurements of Dose Distributions in Small Beams of 6MV X-Rays" by R. K. Rice et al. *Phys. Med. Biol.* vol.32, No. 9 (1987), pp. 1087-1099.

"Development of a Computerized Microstereotaxis Method for Localization and Removal of Minute CNS Lesions Under Direct 3-D Vision" by C. H. Sheldon et al., *Journal of Neurosurgery*, Technical Report, vol. 52, pp. 21-27 (1980).

"A CT-Based Computerized Treatment Planning System for I-125 Stereotactic Brain Implants" by K. Weaver, Ph.D., et al. *J. Radiation Oncology Biol. Phys.*, vol. 18, pp. 445-454 (1989).

"Linear Accelerator as a Neurosurgical Tool for Stereotactic Radiosurgery" by K. R. Winston, M.D., et al. *Neurosurgery*, vol. 22, No. 3 (1988), pp. 454-462.

"A System for Anatomical and Functional Mapping of the Human Thalamus," Thompson, C. J., Hardy, T. L., and Bertrand, G., *Comput. Biomed. Res.*, vol. 19, pp. 9-24 (1977)—textbook.

FIG—1

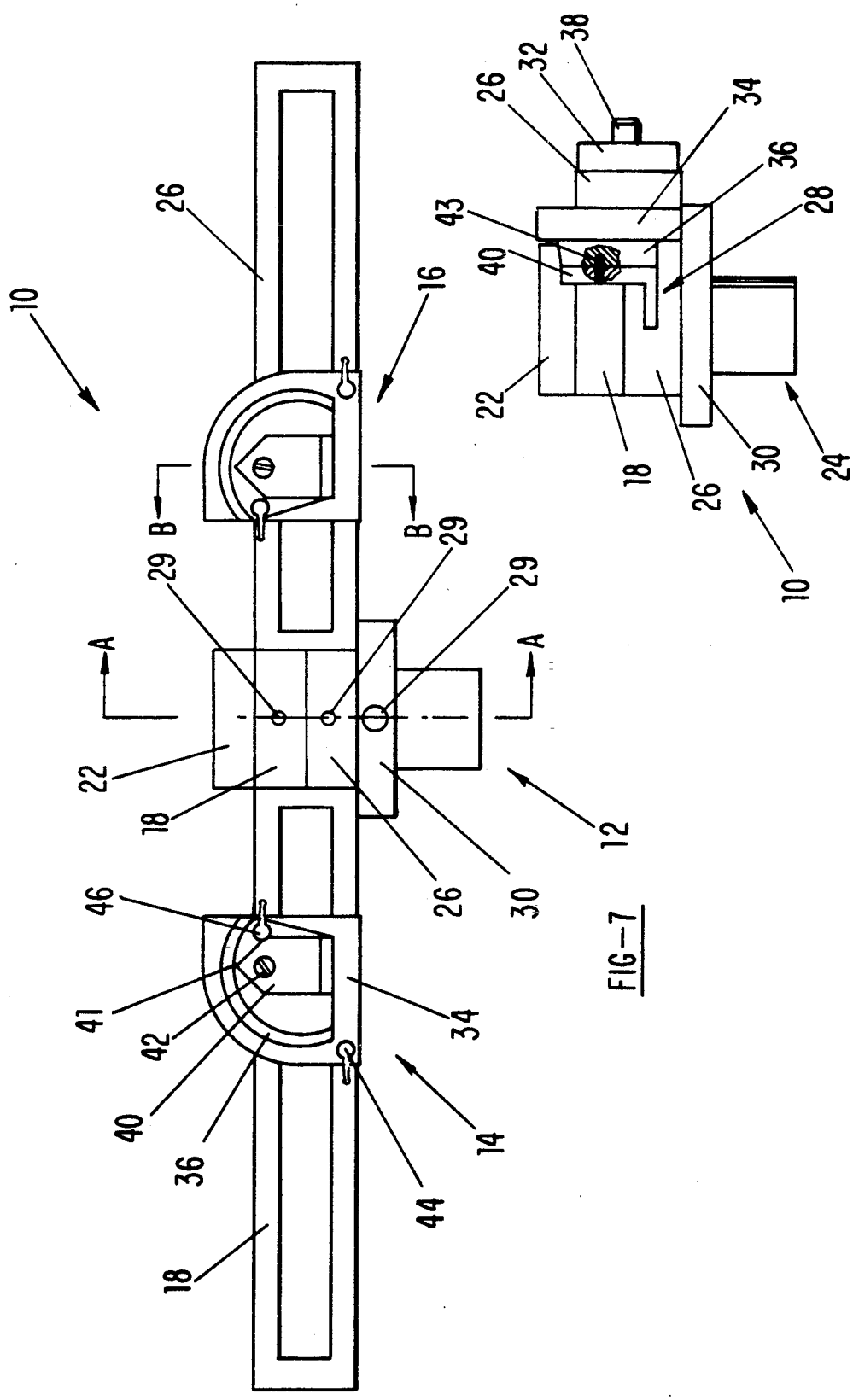

SECTION A-A

SECTION B-B

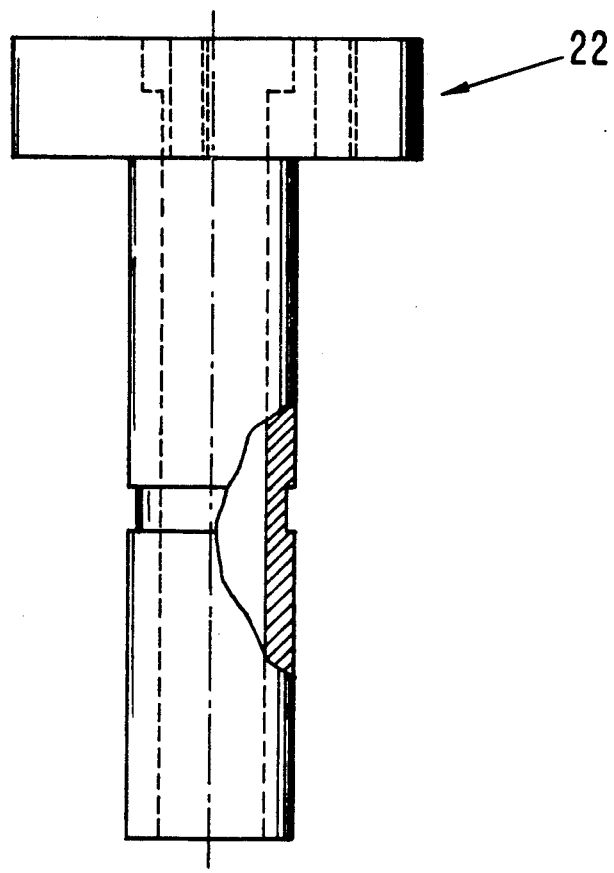
FIG — 13
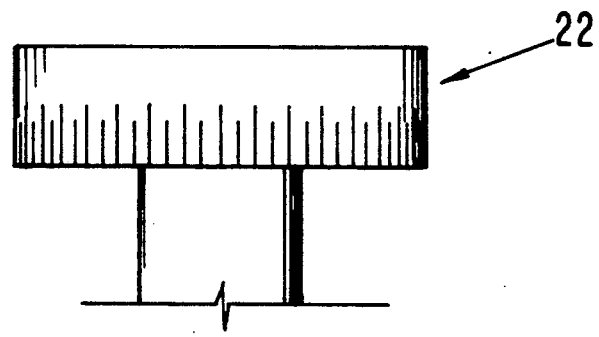
FIG — 14

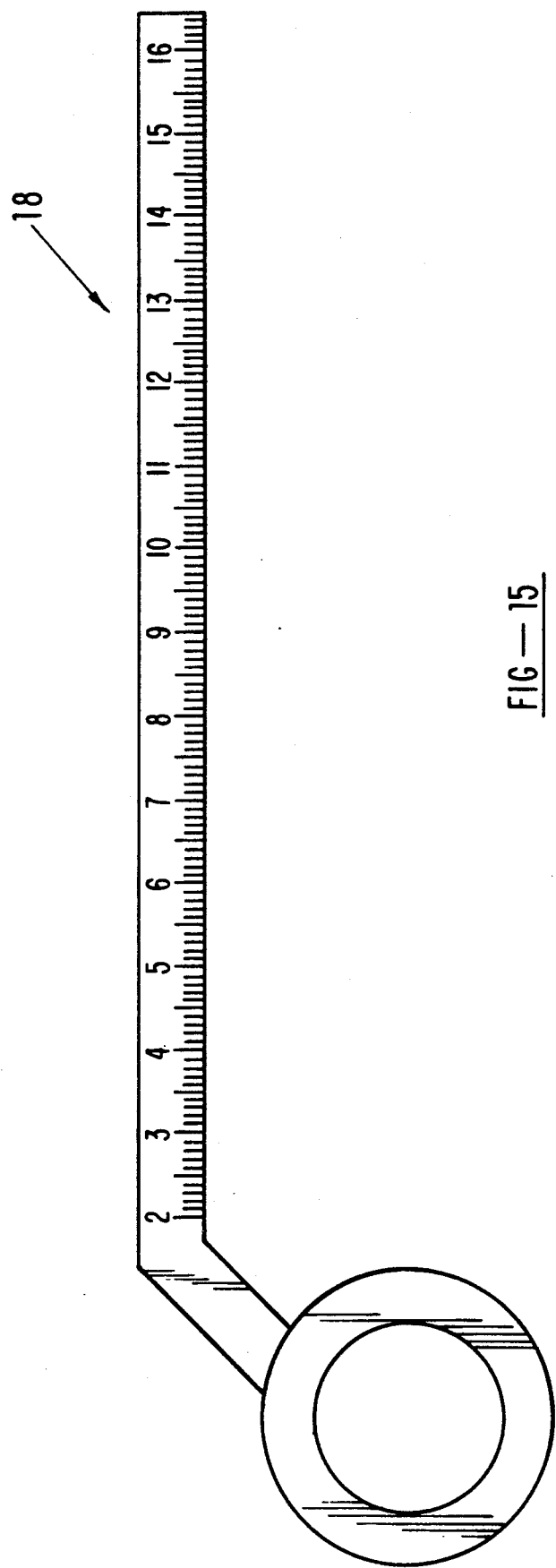
FIG—15

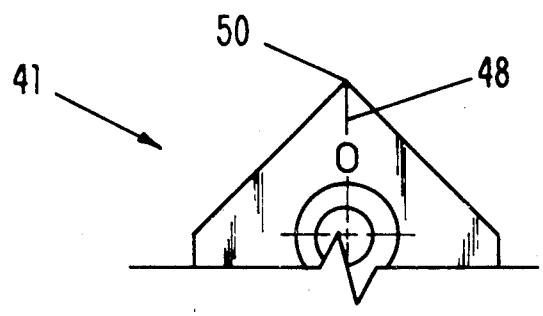
FIG—16
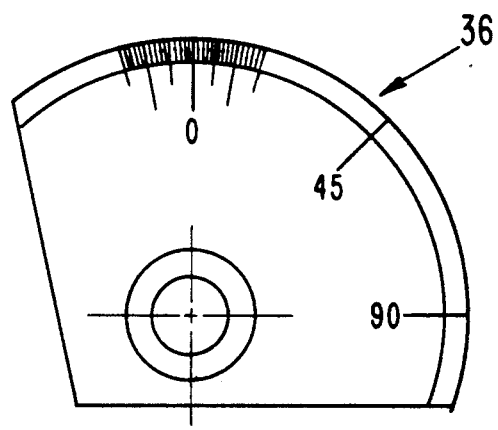
FIG—17
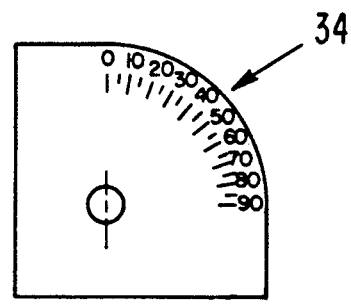
FIG—18

FIG—22

THREE-DIMENSIONAL BEAM LOCALIZATION MICROSCOPE APPARATUS FOR STEREOTACTIC DIAGNOSES OR SURGERY

CROSS-REFERENCE TO A RELATED PATENT APPLICATION

This application is a divisional application of U.S. patent application Ser. No. 07/428,242, filed on Oct. 27, 1989, now abandoned, which is a continuation-in-part application of U.S. patent application Ser. No. 07/290,316, entitled "Method and Apparatus for Video Presentation From a Variety of Scanner Imaging Sources" to Hardy, filed on Dec. 23, 1988, now U.S. Pat. No. 5,099,846, the teachings of which are incorporated herein by reference.

BACKGROUND OF THE INVENTION

1. Field of the Invention (Technical Field)

The present invention relates to a method and apparatus for providing three-dimensional laser localization for stereotactic diagnoses or surgery. The invention comprises a fixed centrally disposed light source and at least one additional movable light source which allows for measurement and calculations of depth, width and position of lesions, tumors, abnormalities, structures, and the like.

2. Description of the Related Art Including Information Disclosed Under 37 C.F.R. §§197-199 (Background Art)

The general types of operative neurosurgical procedures are open operative techniques, stereotactic operative techniques, and a combination of open operative with stereotactic techniques. These are discussed below.

OPEN OPERATIVE TECHNIQUES

Open operative approaches to the brain have been present since antiquity. Typical presently practiced techniques generally involve reflecting the scalp and subcutaneous tissue off of the underlying skull after which a variable size opening to expose the inner cranial contents is subsequently made. The cranial opening is generally tailored to allow adequate instrument access to an intercranial structure and/or lesion. Such techniques require direct visualization of the structure in question. For example, such approaches are commonly used for the localization, identification, and removal of a tumor within the brain itself. A significant difficulty of this approach involves the exact localization and tailoring of the cranial opening for surgical approach and resection of, for example, a tumor. In addition, the exact localization of a lesion in the depths of the brain is frequently not readily apparent from inspection of the overlying brain.

Techniques utilizing various kinds of measurements based on anthropomorphic proportioning in relation to various kinds of diagnostic imaging have been used to approximate the location of intracerebral structures and/or lesions. The location of "large" structures and/or lesions can usually be fairly easily determined with these techniques. This is not true, however, for a "small" deep-seated intracerebral lesion where no telltale evidence of its position is apparent from viewing the overlying cerebral mantel. Other techniques, such as stereotactic surgery, have been used to more precisely indicate the spatial localization of such areas as defined within the confines of a stereotactic surgical frame system.

STEREOTACTIC OPERATIVE TECHNIQUES

The aim of the stereotactic operative technique is to allow physiological exploration and/or destruction of deep cerebral or spinal cord structures which are invisible from the surface, but which location can be determined by a knowledge of their coordinates in space relative to known anatomical and topographical landmarks. The use of stereotaxis in neurosurgical techniques generally seeks to avoid open operative approaches to these areas and cause minimum disturbance to surrounding structures. The technique generally involves the placement of fine electrodes or probes in strategic "target areas," which may be a specific functional anatomical site, a morphological lesion, or an abnormality. Some additional examples are stereotactic radio surgery wherein the principles of stereotaxy are used to project a series of radiation beams into an intracerebral area or lesion.

One of the major difficulties in stereotactic surgery is graphic conceptualization of the location of surgical probes inserted into deep brain structures. Not only is the probe out of the surgeon's sight, but it is tilted, rotated, and extended in many different directions, which makes it almost impossible for the surgeon to maintain a mental picture of where the probe is in the brain core. He must imagine the location of the probe while taking into account the forward and lateral angles of the probe, the distance of the probe from the target, the direction that the electrode extends from the probe, and many other angular variables. Furthermore, the coordinate system of the stereotactic frame seldom corresponds to the "brain coordinate system," thereby causing more room for error and more difficulty in placement of the probe. Traditional stereotactic surgery, therefore, is essentially a "blind" surgical procedure with many complex geometric variables.

COMBINED OPEN OPERATIVE AND STEREOTACTIC OPERATIVE TECHNIQUES

Some of the difficulties inherent in the open operative and the stereotactic operative techniques can be somewhat ameliorated by combining the two techniques in an operative procedure. This has classically been done by the spatial localization of an intracranial structure and/or lesion by the stereotactic localization technique, in which the patient's head is fixed in a stereotactic surgical frame, and the use of a surgical cranial opening tailored to allow adequate direct visualization and access to an intercranial structure and/or lesion. This combined technique, therefore, allows direct visualization of an intracranial structure and/or lesion for surgery. The disadvantage of this technique, as developed to date, has been the three-dimensional volumetric determination of an intracerebral structure and/or lesion in stereotactic space and its shifting position due to gravitational and positional changes of the brain occasioned by its exposure to the atmosphere and the surgical retraction of overlying brain tissue during the course of the subsequent exposure of the underlying brain structure and/or lesion.

Several methods of combined open operative and stereotactic technique have been developed for the localization and resection of intracerebral structures and/or lesions. The following publications set forth examples of the such general principles of localization:

1. Kelly, P. J., Alker, George J., Jr., and Georss, Stephan, "Computer-Assisted Stereotactic Laser Microsurgery for the Treatment of Intracranial Neoplasms,", *Neurosurgery*, Vol. 10, pp. 324–331 (1982).

2. Koslow, M. Abele, M. G., Griffith, R. C., Mair, G. A., and Chase, N. E., "Stereotactic Surgical System Controlled by Computed Tomography," *Neurosurgery*, Vol. 8, pp. 72–82 (1981).

3. Shelden, C. H., McCann, G., Jacques, S., Luter, H. R., Frazier, R. E., Katz, R., Kuki, R., "Development of a Computerized Microstereotaxis Method for Localization and Removal of Minute CNS Lesions Under Direct 3-D Vision," *Journal of Neurosurgery*, Technical report, Vol. 52, pp. 21–27 (1980).

4. A stereotactic helium neon laser light pointer distributed by A.B. Elekta Instruments.

The techniques involved in these publications herein noted consist of the following:

1. A stereotactic frame system fixable about a patient's head is used in conjunction with various imaging technologies, e.g., plain X-ray, computerized tomographic scans, magnetic resonance imaging scans, and stereotactic angiography, to locate deep seated intracerebral lesions and stereotactic space.

2. Various stereotactic volumetric determinations with transformation algorithms have been used to simulate the position of the tumor in the stereotactic space. These, however, do not take into consideration positional and gravitational shifts of a lesion as noted above.

3. Many current techniques incorporate a laser light pointer along the course (tract) in which a surgeon might encounter a lesion or tumor. The position of the tumor, however, frequently varies from its original position as determined from various types of diagnostic imaging, due to patient position, e.g. sitting up or lying down, pressure changes, and the like. No good marker prior art techniques have been developed to accurately define the tumor margins (which are subsequently used to determine tumor volume) or to compensate for positional shifts of a tumor or lesion.

Several patents disclose methods and devices which are attempts to better localize a tumor, or the like, using a stereotactic frame. None, however, provide the three-dimensional accuracy of the present invention, nor utilize the localization method and apparatus of the present invention. These patents are discussed below.

U.S. Pat. No. 3,508,552, entitled *Apparatus for Stereotaxic Neurosurgery*, to Hainault, et al., discloses the use of multiple grids for use in conjunction with an x-ray device to determine a passage for the surgeon to enter the brain. U.S. Pat. No. 4,350,159, entitled *Frame for Stereotactic Surgery*, to Gouda, teaches the use of radioopaque vertical markers on a stereotactic frame for alignment purposes.

U.S. Pat. Nos. 4,638,798, entitled *Stereotactic Method and Apparatus for Locating and Treating or Removing Lesions*, to Shelden, et al., and 4,706,665, entitled *Frame for Stereotactic Surgery*, to Gouda, both disclose a procedure and apparatus for locating and removing a brain tumor using a series of CT scans to locate the tumor and an adjustable stereotactic frame to support probes and instruments in a three-dimensional arrangement, indicated by the scans.

French Patent 2384481, entitled *Stereotaxic Apparatus*, to Hubert, et al., discloses the use of a laser and mirrors to align the X-ray beam, useful in medical stereotaxy.

None of the above-described methods or devices are able to translate to the surgeon the three-dimensional boundaries of the lesion as resection takes place.

Co-pending application Ser. No. 07/290,316, entitled *Method and Apparatus for Video Presentation From a Variety of Scanner Imaging Sources*, filed on Dec. 23, 1988, to Hardy, relates to a three-dimensional stereotactic technique, utilizing various scanner imaging sources, to assist a surgeon or health practitioner in locating and measuring lesions, tumors, abnormalities, structures, and the like. The '316 application is useful in conjunction with the present invention.

SUMMARY OF THE INVENTION (DISCLOSURE OF THE INVENTION)

The present invention relates to a stereotactic surgical laser localization apparatus attachable to a stereotactic frame. The apparatus comprises means for emitting at least two (and preferably three or more) light beams from separate and spaced points; means for attaching the light beam emitting means on a frame; means for movably adjusting the relative positions to one another of the light beam emitting points; means for aiming the light beams at user selected locations on a body; and means for ascertaining desired information about a selected volumetric entity of the body from the positions of the light emitting means in the apparatus, the relative positions to one another of the light emitting means, and the aiming directions of light beams from the first and second light beam emitting points. The mounting frame is attached to the stereotactic frame. The light beam emitting means may be positioned on the mounting frame along an arc or tangent of the stereotactic frame, in a linear, spherical, or planar relationship.

Desired information about the selected volumetric entity of the body is determined by proportional angulation methods using information about the positions of the light beam emitting sources on the frame, the positions of the light beam emitting sources relative to one another, and the aiming directions of the light beams from the light beam emitting sources. Information about a point, area or volume of the volumetric entity can be determined by using a series of selected data points.

In the preferred embodiment, there are at least three light emitting sources, with one of such light emitting sources being a fixed, centrally disposed light emitting source, with the additional light beam emitting sources being movably adjustable, spaced from and independent of one another and the fixed centrally disposed light source. The fixed centrally disposed light beam is aimed at a predetermined, fixed location of the selected volumetric entity of the body. The additional light beams are variably aimed at additional selected locations of the selected volumetric entity of the body. The additional light beam emitting sources are movably adjustable by micrometer positioning or by digital means.

In the preferred embodiment, the apparatus comprises a separate wing member for each of the additional light beam emitting sources, with the light beam emitting source longitudinally movable on the wing member and pivotally movable such that the beams emitted therefrom can move between a 0° to 90° arc relative to the fixed centrally disposed light beam. One or more of the wing members are rotatable, up to 360°, about the fixed centrally disposed light beam emitting means.

The preferred light beam emitting source comprises a laser, with fiber optics connections. Alternatively, the light beam emitting source comprises laser diodes.

In an alternative embodiment, the invention comprises a stereotactic surgical laser localization apparatus disposed within a surgical microscope. This apparatus comprises means disposed within the surgical microscope for emitting at least two light beams from two separate and spaced points; means for movably adjusting the relative positions to one another of the light beam emitting points; means for aiming the light beams at user selected locations on the selected volumetric entity of the body; and means for ascertaining desired information about the selected volumetric entity of the body from the positions of the light emitting sources in the apparatus, the relative positions to one another of the light emitting sources, and the aiming directions of light beams from the light beam emitting points. Prism means disposed within the surgical microscope are useful in this embodiment. The light beam emitting sources may be disposed on the objective mount of the surgical microscope, in a spherical relationship to one another.

The invention further comprises a method of determining desired information about a volumetric entity in a body. This method comprises the following steps:

a) positioning a plurality of light beam sources on an apparatus fittable on the body;

b) adjusting the spacing and the rotational positions of the beam sources relative to one another so that the beams emitted therefrom intersect at a point on the volumetric entity of the body; and c) using proportional angulation, determining positional information about the entity.

Steps b) and c) may be repeated a multiplicity of times to a series of points on an area or volume of the volumetric entity to determine positional, area, and volumetric information about the volumetric entity.

Accordingly, it is a primary object of the present invention to localize and determine the fixed, varying or changing position of selected lesions, tumors, abnormalities, structures, and the like, in a body.

It is another object of the present invention to measure and calculate the widths, depths, and positions of selected lesions, tumors, abnormalities, structures, and the like, in a body.

Yet another object of the present invention is to provide an apparatus for stereotactic surgery, which can be attached to a stereotactic frame or utilized with a stereotactic microscope.

Additional objects, advantages and novel features of the invention will be set forth in part in the description which follows, and in part will become apparent to those skilled in the art upon examination of the following or may be learned by practice of the invention. The objects and advantages of the invention may be realized and attached by means of the instrumentalities and combinations particularly pointed out in the appended claims.

BRIEF DESCRIPTION OF THE DRAWINGS

The accompanying drawings, which are incorporated into and form a part of the specifications, illustrate several embodiments of the present invention and, together with the description, serve to explain the principles of the invention. In the drawings:

FIG. 7 is a front view of the preferred frame system of the present invention;

FIG. 8 is an end view of the frame system of FIG. 7;

FIG. 13 is a side plan view of the shaft of FIG. 7;

FIG. 14 is a side view of the shaft of FIG. 7 showing markings;

FIG. 15 is a top view of one of the side horizontal wings of FIG. 7, showing markings;

FIG. 16 is a front view of one of the pointers of the invention of FIG. 7, showing a marking;

FIG. 17 is a front view of one of the vertical azimuth bezels of FIG. 7, showing markings;

FIG. 18 is a front view of one of the horizontal bezel carriages of FIG. 7, showing markings;

Figure 1:
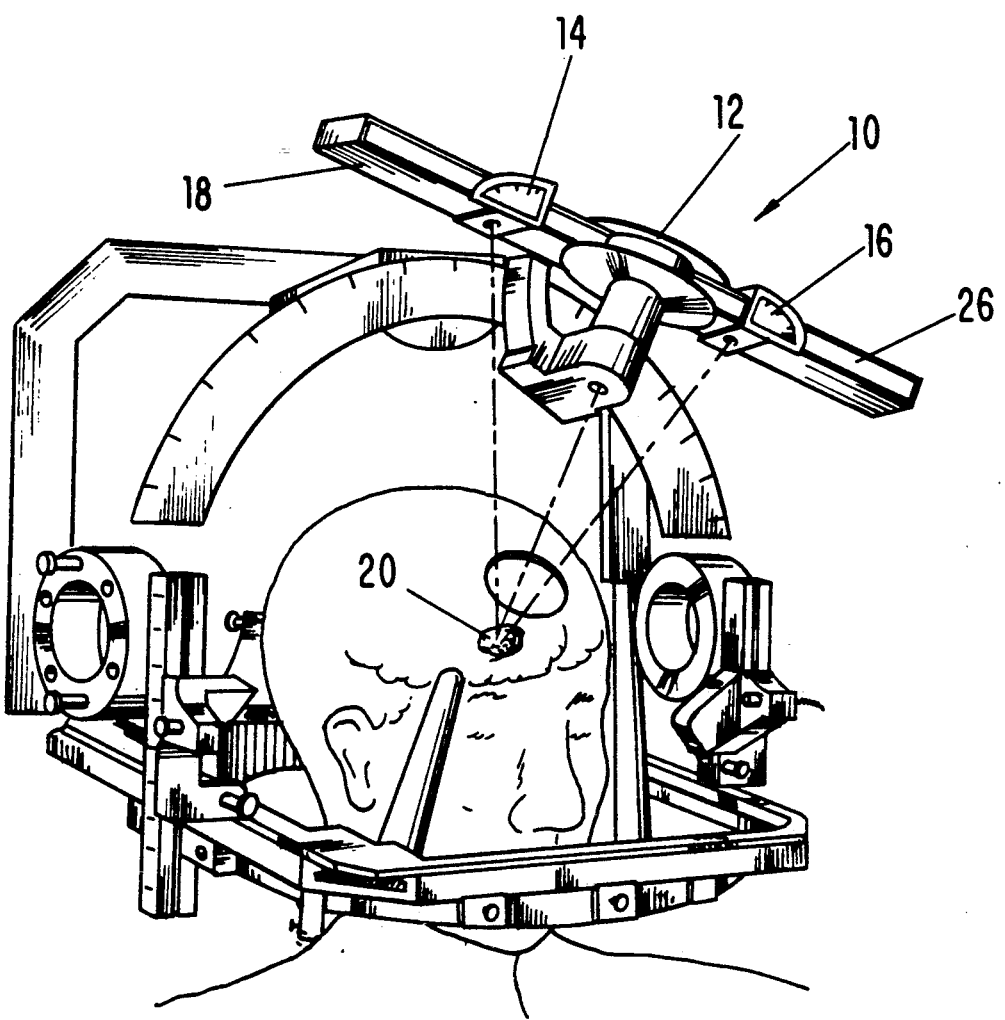
FIG. 1 is a perspective view of the preferred laser localization apparatus of the present invention showing a fixed centrally disposed light source, and two additional light sources.

DETAILED DESCRIPTION OF THE PREFERRED EMBODIMENTS OF THE INVENTION (BEST MODE(S) FOR CARRYING OUT THE INVENTION)

The laser localization apparatus and method of the present invention utilize several spaced light sources for three-dimensional localization and measurement of lesions, tumors, abnormalities, structures, and the like (generally referred to herein as "lesions" or "tumors"), in a selected part of a human or animal body, particularly in a brain, (generally referred to in the specification and claims as "entity", "volumetric entity" or "area to be measured" or "volume to be measured" or "brain"). The invention is particularly useful in conjunction with a medical stereotactic frame. Although the term "stereotactic frame" is customarily used in the art to denote a stereotactic frame attachable to a head, this term, for the purposes of the present invention, means a frame which is attachable to any part of the body. The invention is not limited to surgical or diagnostic methods for the head or brain, but can also be used on other parts of the body, e.g. the spine, with a frame system suitable for such body parts (e.g. a cylindrical coordinate system for a spinal stereotactic frame).

The invention involves a central light beam from a light emitting source, such as a laser, which is projected along a previously determined stereotactic radian along the course of which the selected volumetric entity of the body may be located. Adjacent to this central light source are several (preferably at least two) additional side light emitting sources which emit "side light beams"), such as laser beams, which are projected from known positions relative to the central light source. Such positioning depends upon the structure of the stereotactic frame system. For example, in a spherical coordinate system the additional light emitting sources can be located along either a tangent to the arc or an arc of a stereotactic frame. The side light sources are moveable along such arcs or tangents so that they can be positioned accurately in relationship to the central light source. The central light beam and the side light beam can originate from a single source and by using optical equipment, such as mirrors, prisms, and lasers, can be made to project from three spaced points. The beams can alternatively originate from two, three or more sources and rely on mirrors, prisms, or lasers. Laser diodes can be used to provide the light beams. The angles of the side beams are variable in a number of fashions so that they can be made to intersect the central light beam at varying points along the central light beam's trajectory. This capability allows calculations of depths along the trajectory of the central light beam for determining the near and far positions of the volume of the selected volumetric entity of the body, such as an intracerebral structure and/or lesion, in three-dimensional space. Such calculations are performed by proportional angulations. Also derived from the ability to vary the angles of the additional or side light beams is the capacity to determine the projected boundaries of the volume of the lesion in three-dimensional space in a full spherical manner. Measurements of a three-dimensional volume can be determined from various angles of beam intersection as discussed below.

FIGS. 1-18 illustrate a preferred embodiment of a localization laser apparatus of the present invention comprising a frame system 10 having a centrally disposed, fixed light source 12 and two moveable side light sources 14 and 16 disposed on side horizontal wings or tracks 18 and 26, which are attachable to a stereotactic frame (see FIG. 1). The stereotactic frame may be one which is commonly available in the art. Centrally disposed light source 12 is preferably mounted in a fixed, centrally disposed position. Side light sources 14 and 16 each have horizontal motion along the horizontal tracks 18 and 26 independent of centrally disposed light source 12 and each other. Also as demonstrated in the drawings, light sources 14 and 16 are each independently, pivotally moveable in order to enable the surgeon or health practitioner to change the angle of each of their respective laser localization beams from a vertical aim through a 90° arc crossing the fixed vertical beam from light source 12. The light beams emitted from light sources 12, 14, and 16 are shown by dashed lines in the drawings.

Figure 2:
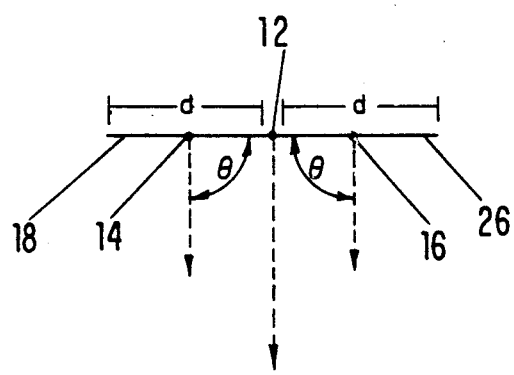
FIG. 2 is a diagram of the invention showing horizontal laser tracks with a fixed centrally disposed light source and two additional light sources.

FIGS. 2-6 illustrate, simply, how side light sources 14 and 16 (shown as points and also sometimes referred to as "points" in the specification and claims) move pivotally relative to centrally disposed, fixed light source 12 (also shown as a point) in the localization of a hypothetical tumor 20 (shown by a round circle). FIG. 2 illustrates all light beams from the light points or sources 12, 14, and 16 having a vertical aim. As can be readily seen, the side light sources 14 and 16 can pivot through a 90° arc (shown by the angle Θ markings on FIG. 2). FIG. 2 also illustrates a range of possible horizontal movement (denoted as "d") for the side light sources 14 and 16, relative to the centrally disposed light source 12, along the side horizontal tracks 18 and 26 (shown by lines).

Figure 3:
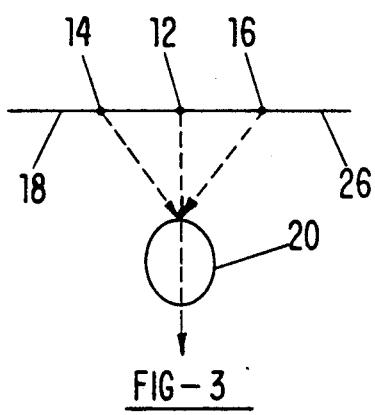
FIG. 3 is a diagram of the invention of FIG. 2 showing the localization of the top of a tumor.
Figure 4:
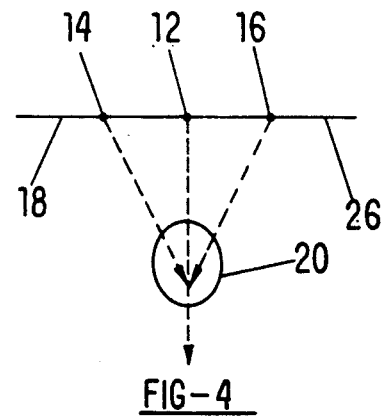
FIG. 4 is a diagram of the invention of FIG. 2 showing the localization of the bottom of the tumor.
Figure 5:
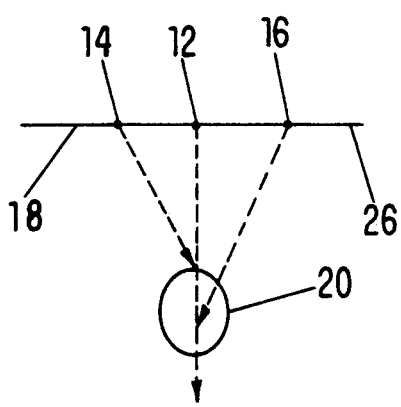
FIG. 5 is a diagram of the invention of FIG. 2 showing an alternative localization of the top and bottom of a tumor.
Figure 6:
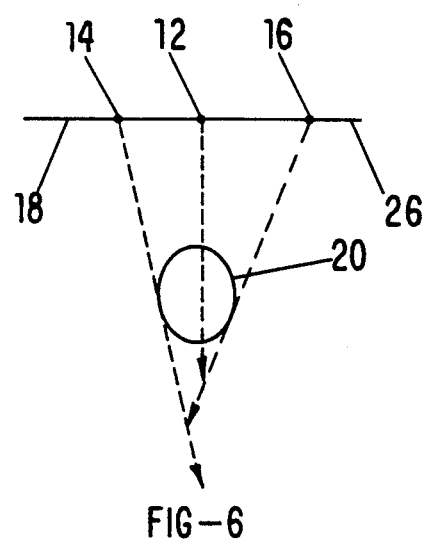
FIG. 6 is a diagram of the invention of FIG. 2 showing the localization of the sides or the width of the tumor.

FIGS. 3-6 illustrate the intersection of the light beams for the localization of the tumor 20. In this example, centrally disposed light source 12 has its light beam aimed at the center of the tumor 20. Side light sources 14 and 16 emit beams which intersect with the central beam from light source 12 to define the top, bottom, sides and general positioning of the tumor 20. FIG. 3 illustrates beams from side light sources 14 and 16 intersecting the beam from centrally disposed light source 12 to define the top of the tumor 20. FIG. 4 illustrates beams from side light sources 14 and 16 intersecting the beam from centrally disposed light source 12 to define the bottom of the tumor 20. FIG. 5 illustrates an alternative method of defining the top and bottom of the tumor 20 with the intersection of the side beams with the central beam. FIG. 6 illustrates beams from side light sources 14 and 16 intersecting with the central beam from light source 12 to define the edges or sides of the tumor 20. Side light sources 14 and 16 are rotatable on a tangential plane all or a portion of 360° around central light source 12. Hence, tumors or lesions of varying widths can be measured and located. Although these diagrams illustrate generally a two-dimensional working of the invention, those skilled in the art can appreciate that the side light sources 14 and 16 are independently rotatable all or a portion of 360° on a tangential plane around the central light source 12 and that more than two additional or side light sources may be utilized in practicing the invention (e.g. see FIG. 19) to provide more precise localization and measurements. Likewise, a centrally fixed light source and one additional light source or two variable light sources (with no centrally fixed light source) may be used to practice the invention, using proportional angulation methods to make determinations, although such determinations will not be as precise as those obtained by utilizing three or more light sources.

All measurements are easily determined using well known proportional angulation techniques, by knowing the distance of the point of intersection of each of the beams, the angles of the beams, and the rotations of the light sources. Such calculations can be performed manually, or preferably with interactive software, and can be incorporated into or used in conjunction with other stereotactic methods and apparatuses, such as those disclosed in co-pending patent application, Ser. No. 290,316.

The present invention, using angulational determinations of three-dimensional spatial volumetrics and position can aid the surgeon or health practitioner to: (1) directly indicate the position of e.g. an underlying intracranial/intracerebral structure, such as a lesion or tumor within the confines of the skull, so that the size and position of an opening, such as a cranial opening, can be accurately tailored; (2) accurately determine the location of the lesion or tumor; (3) accurately determine for simulation with computer graphics simulation methodology, gravitational and positional shifts of the lesion or tumor; and (4) accurately measure the depth, width, and volume of the tumor or lesion. Desired information about the tumor is determined by proportional angulation methods using information about the positions of the light sources, the positions of the light sources relative to one another, and the directions of the light beams from the light sources. Information about a point, area or volume of the tumor can thereby be determined using a series of selected data points.

A preferred three-dimensional laser localization apparatus is shown in the perspective view of FIG. 1, and in greater detail in the plan views of FIGS. 7-18. As shown therein, the frame system 10 of the invention is attachable as a separate apparatus onto a stereotactic probe holder device or on a typical stereotactic frame. The present invention comprises a central light emitting source 12, such as a laser light source, and two or more additional or side light emitting sources 14 and 16 which are independently movable away from and towards the central light emitting source 12, along a tangent bar or arc of the frame system 10, such as on a horizontal wing or track 18 and 26. The side light sources 14 and 16 can be moved along a tangent or an arc carrier anywhere within a tangential plane or arc relative to the central light source 12. The side light sources 14 and 16 are also preferably adjustably variable in an angular or pivotally rotatable fashion by micrometer or digital positioning so that their relationships of beam intersection with the beam from the central light source 12 can be varied or changed within highly accurate parameters.

Figure 9:
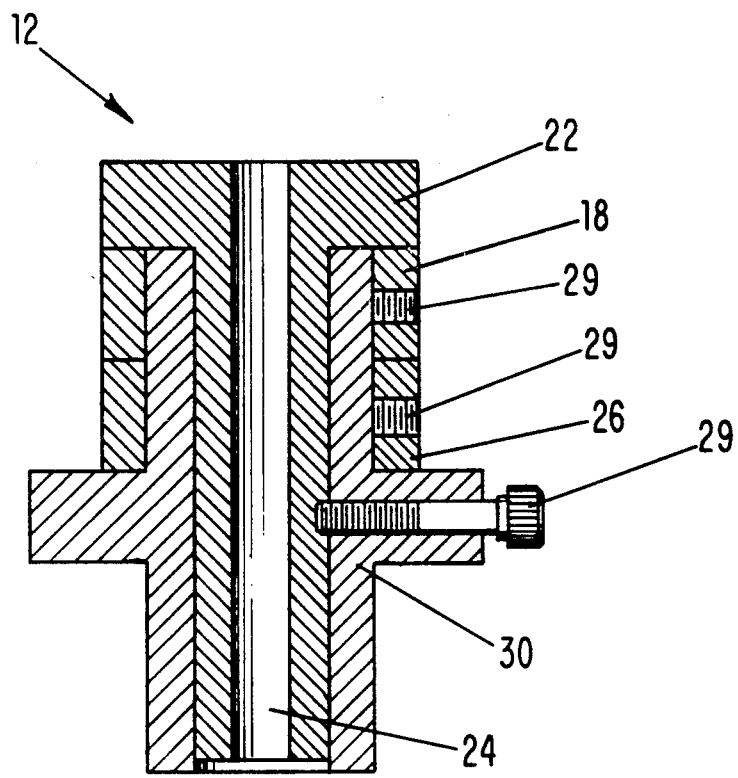
FIG. 9 is a cross-sectional view along section A—A of FIG. 7.
Figure 10:
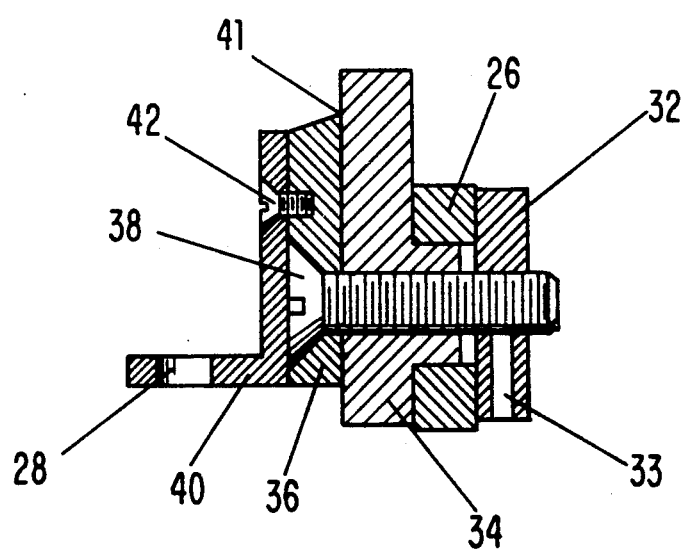
FIG. 10 is a cross-sectional view along section B—B of FIG. 7.

FIGS. 7 and 8 illustrate front and side views, respectively, of the preferred frame system 10 of the invention. FIGS. 9 and 10 illustrate cross-sectional views of sections A—A, and B—B, respectively, of FIG. 7. The two ends or sides of the frame system 10 are substantially similar and thus the discussion below which is applicable to one end only is also applicable, in general, to the other end. The frame system 10 comprises a centrally disposed shaft system 22 for mounting the central, fixed light source 12 and allowing the centrally disposed fixed light beam emitted therefrom to be emitted via central light emitting channel 24 (see FIGS. 8 and 9); and side horizontal wings 18 and 26 for mounting the side light sources 14 and 16 and allowing the light beams emitted therefrom to be emitted via separate light emitting channels 28 (see FIGS. 8 and 10). As shown in FIG. 8, the vertical aim of all light beams is preferably aligned. FIG. 9 shows the central shaft 22 affixed to the frame system 10 by various set screws 29. The side horizontal wings 18 and 26 are independently rotatably and movably mounted above a spindle 30. FIG. 10 shows the relationship among a locking plate 32 with set screw 33, the side horizontal wing 26, a horizontal bezel carriage 34, a vertical azimuth bezel 36, a pivot screw 38, a focusing lens assembly bracket 40 which carries the side light emitting channel 28, and a holding screw 42. A holding pin 43 assists in holding the vertical azimuth bezel 36 to the focusing lens assembly bracket 40 (see FIG. 8). The focusing lens assembly bracket 40 which is fixed relative to the vertical azimuth bezel 36, can pivot, as adjusted by the surgeon, relative to the horizontal bezel carriage 34 which is affixed to the side horizontal mounting wing 18 or 26 and the locking plate 32. A sloped pointer 41 shows the surgeon the angle of the beam being emitted from the light emitting source 16 via the side light emitting channel 28. Holding screw 44 holds the vertical azimuth bezel 36 and horizontal bezel carriage 34 in place along the horizontal wing 18 or 26 after the desired position is obtained. Holding screw 46 holds the focusing lens assembly bracket 40 and vertical azimuth bezel 36 in position relative to the horizontal bezel carriage 34 after the desired angle position is obtained.

Figure 11:
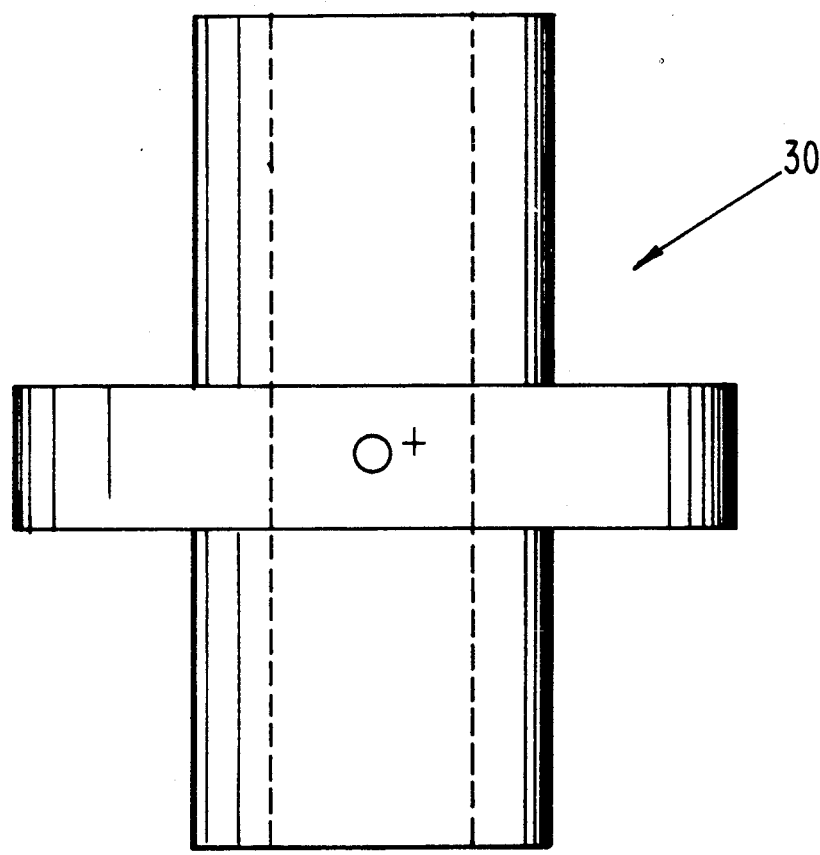
FIG. 11 is a side plan view of the spindle of FIG. 7.
Figure 12:
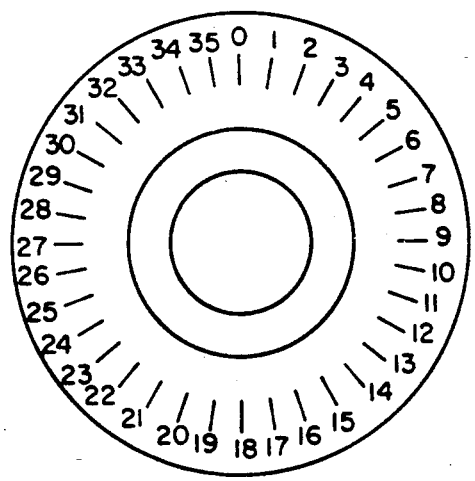
FIG. 12 is a top view of the spindle of FIG. 7 showing markings.

FIG. 11 shows a side view of the spindle 30 and FIG. 13 shows a side view of the central shaft 22 of the preferred embodiment of the invention (also see FIGS. 8 and 9). The spindle 30 is rotatably disposed within the central shaft 22 (see FIG. 9). The horizontal wings 18 and 26 (see top view in FIG. 15) are rotatably disposed around the spindle 30 (see FIG. 9). Markings, preferably showing a 360° rotation, are present on the top of the spindle 30, as shown in FIG. 12. Likewise, markings may be present on the side of the central shaft 22, such as shown in FIG. 14, and on the horizontal side wings 18 and 26, such as shown in FIG. 15.

More detailed drawings of some of the members shown in FIG. 10 are shown in FIGS. 16-18. The pointer 41 of the focusing lens assembly bracket 40 may have a vertical line 48 at the apex 50, as shown in FIG. 16. Likewise, the vertical azimuth bezel 36 may have Vernier scale markings, such as shown in FIG. 17. Similarly, the horizontal bezel carriage 34 may have Vernier scale markings, such as shown in FIG. 18. All of these markings, including the markings on the spindle 30, the central shaft 22 and the side horizontal wings 18 and 26, assist the surgeon or health practitioner to accurately take measurements and thereby determine the location and volume of the tumor or lesion.

Figure 19:
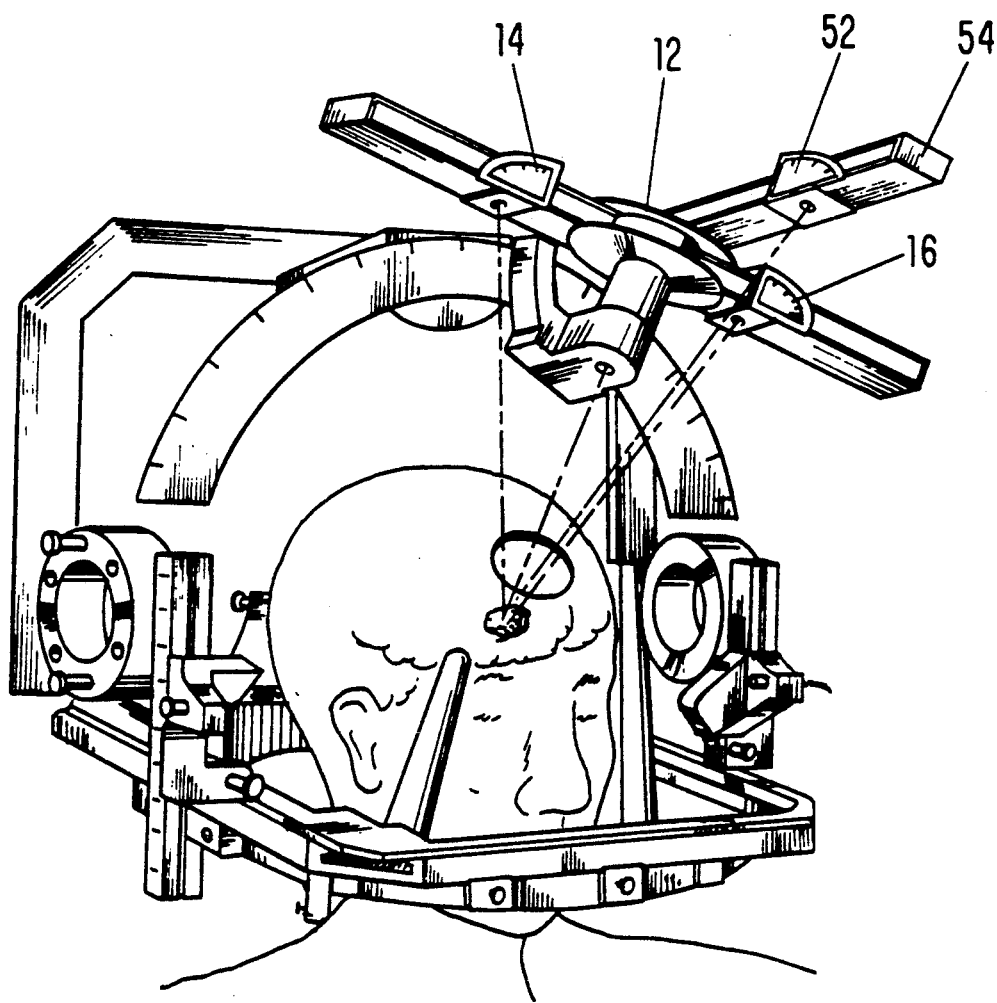
FIG. 19 is a perspective view of the laser localization apparatus of the present invention showing a fixed centrally disposed light source and three additional light sources.
Figure 20:
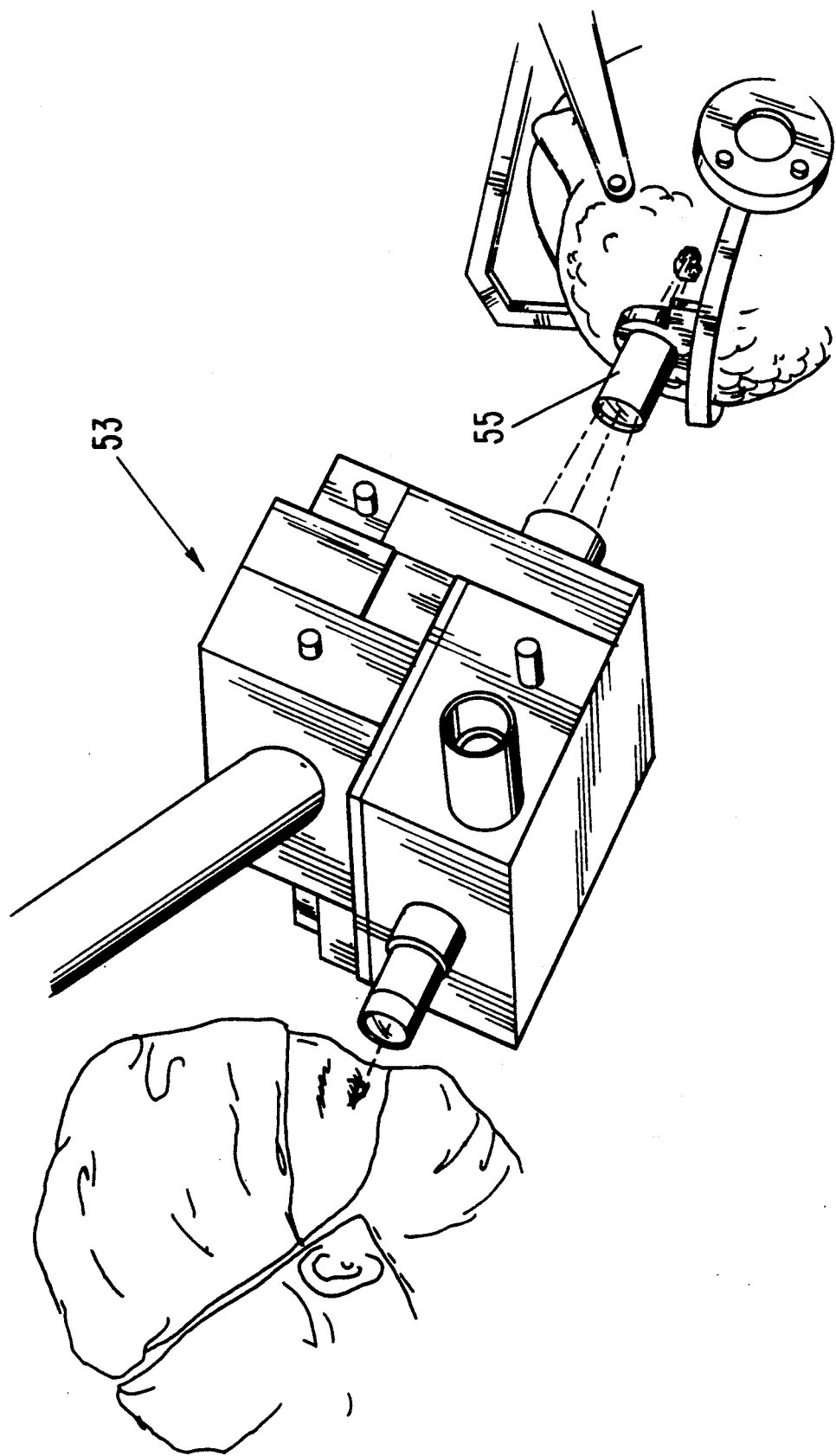
FIG. 20 is an alternative microscope embodiment of the invention.

FIG. 19 illustrates an alternative embodiment of the invention, wherein there are three "side" light sources 14, 16, and 52, in addition to the centrally disposed light source 12. All of the discussion above pertains to this alternative embodiment, except there is an additional wing 54 which comprises the third side light source 52. The additional light source 54 enables the practitioner to make even more accurate determinations and measurements. As can be appreciated by those skilled in the art, the invention is not limited to three or four spaced light sources, but may comprise as many light sources as the practitioner may desire to make accurate determinations and measurements.

In yet another alternative embodiment, as shown in FIGS. 20-23, the three-dimensional laser localization apparatus for stereotactic surgery is attached to and incorporated within the optics of a surgical dissecting microscope 53. This embodiment requires that the microscope objective lens 55 be attached to the arc carrier of the stereotactic surgical frame. This embodiment allows for smaller openings, such as for cranial and cerebral openings, for surgical approach to deep-seated intracranial or intracerebral structures and/or lesions.

In this embodiment, the laser light sources are delivered by an optical prismatic system designed such that the primary laser light source is split into at least three separate laser light beams (shown by dashed lines) which project from the microscope's objective lens 55. The prismatic system is designed such that by micrometer and/or digital adjustments the additional (preferably at least two) laser light sources are movable around at an angle in relation to the central laser light beam.

Figure 21:
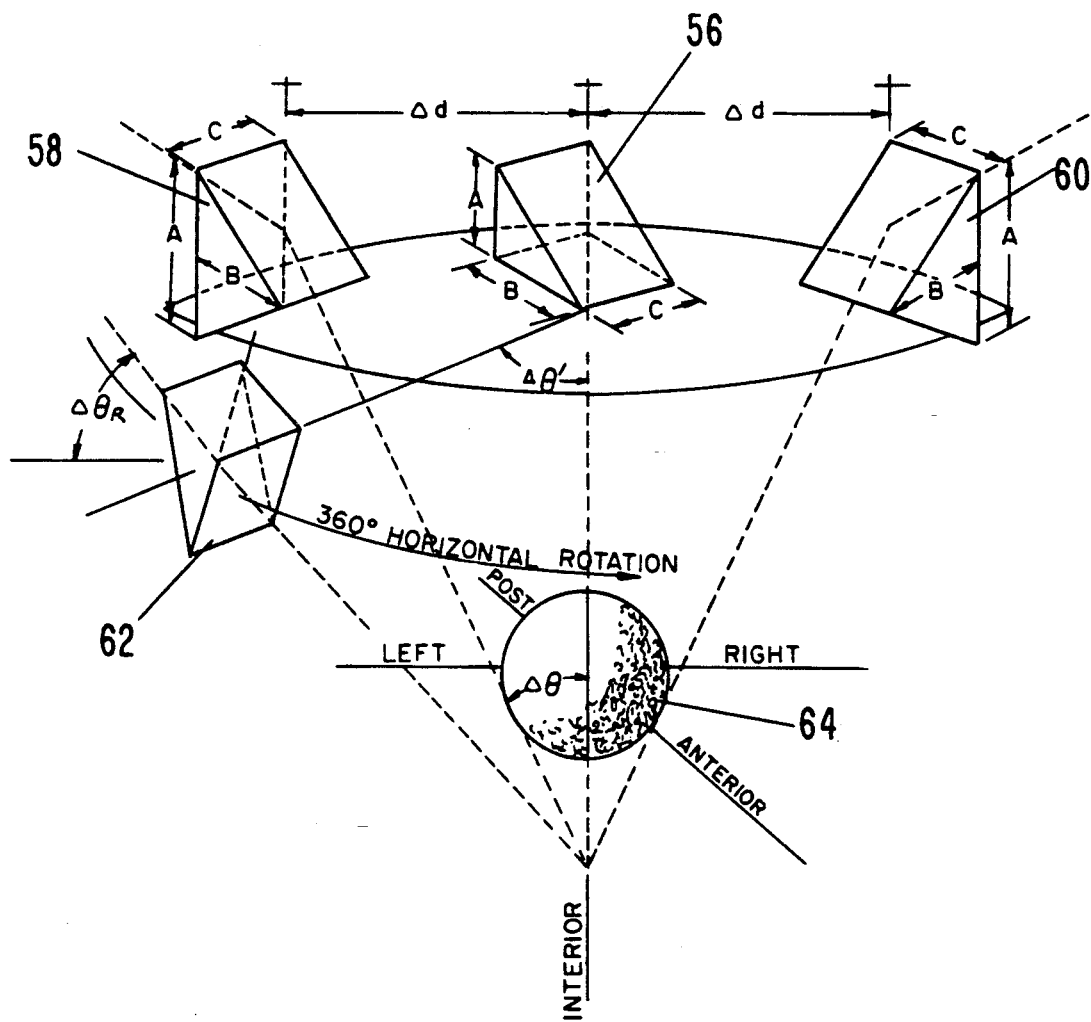
FIGS. 21-23 are diagrams of the light source and prism operation within the microscope embodiment of FIG. 20.
Figure 22:
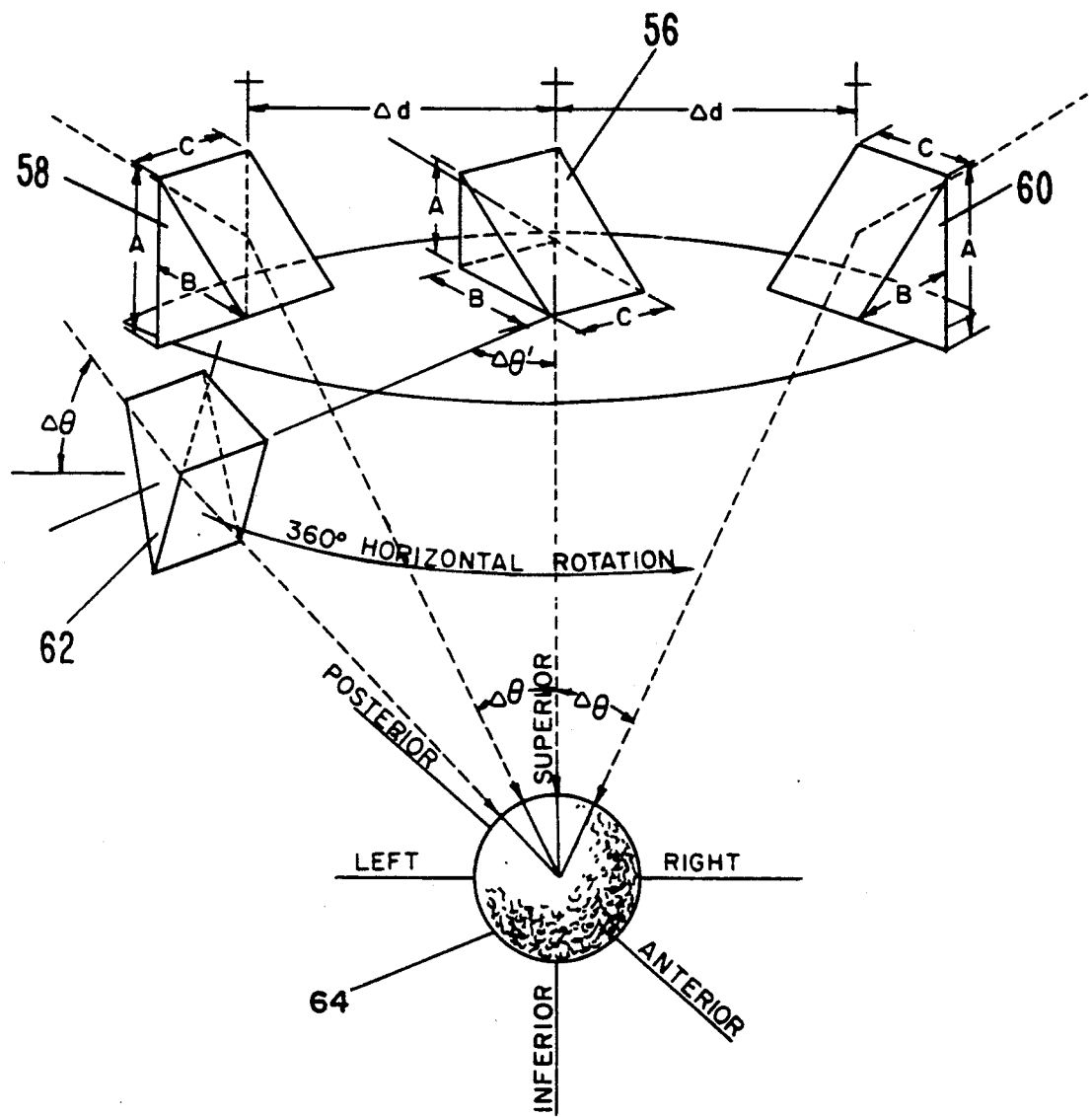
Figure 23:
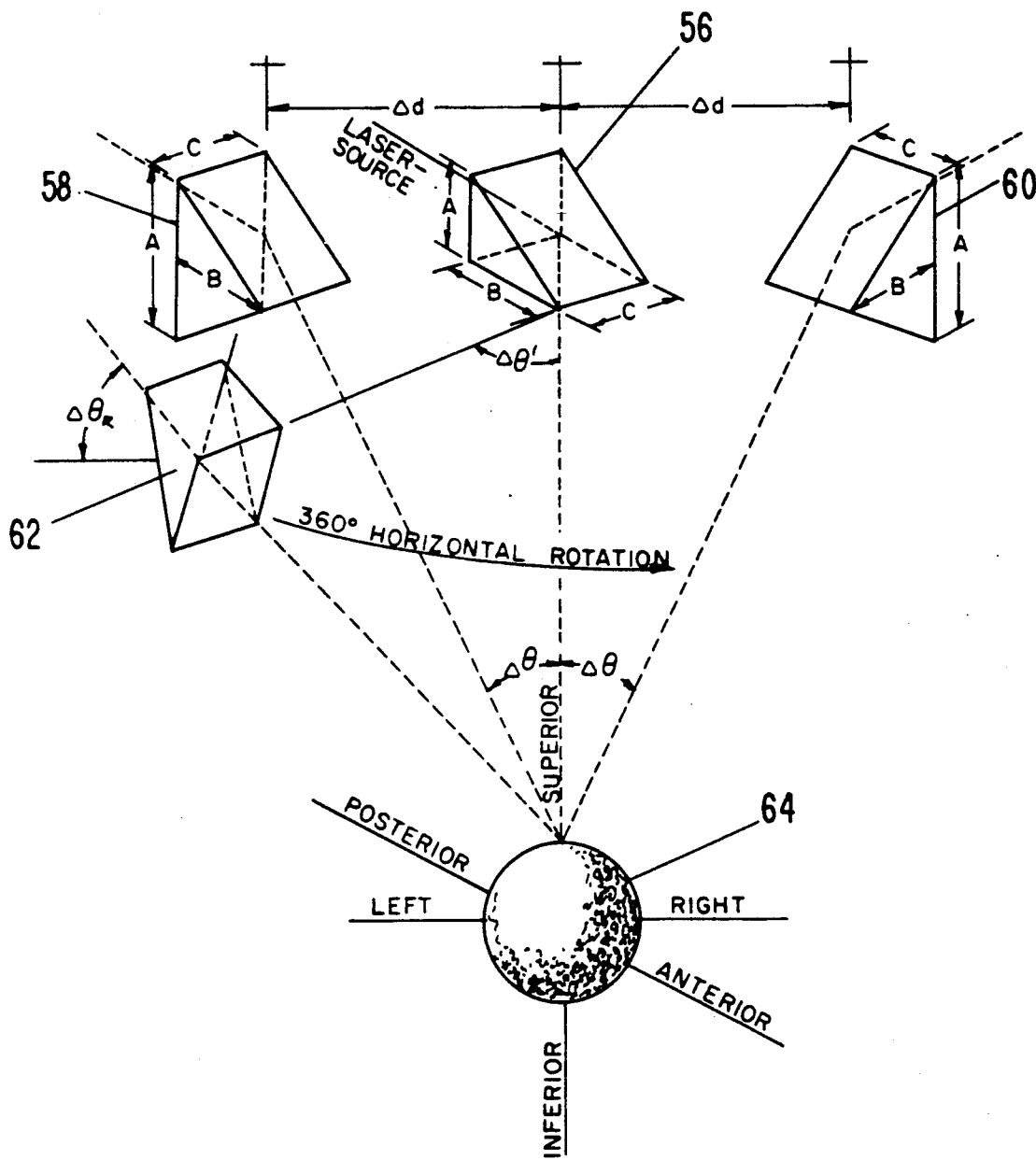

FIGS. 21-23 schematically show the relationships, in this alternative embodiment, among a fixed position light source 56; a first additional variable light source 58, preferably with micrometer or digital adjustment along axes A, B, and C; a second additional variable light source 60, preferably with micrometer or digital adjustment along axes A, B, and C; a rotation prism 62; and a hypothetical tumor 64. FIGS. 21-23 illustrate the localization of the sides, center and top of the tumor 64, respectively, by the angular rotation of the prism 62 (preferably 360°), the angles between the laser beams, shown as "ΔΘ", "ΔΘ''''", and "ΔΘ$_R$", and the distance between the light sources on the microscope objective mount, shown as "Δd" in these figures. As can be appreciated by those skilled in the art, this microscope embodiment may comprise more than two additional variable light sources, such as discussed with reference to the preferred embodiment.

The preferred light source, in accordance with the present invention, is a laser light source. The light beams can be transmitted by means common to the art, preferably by either one of two fashions. The laser may be connected by special optic coupling to fine fiber-optic cabling to which a lens system is attached to the associated fiber-optic cabling for projecting the laser light beam. One such fiber-optic laser light linkage for each laser light source is attached to the laser light carrier on the stereotactic frame system 10. Or, the primary source of all laser light may be from miniaturized laser diodes having the laser light source and lens system incorporated into the laser diodes for projection of the laser light. These sources are connected by special coupling to the laser light carrier on the stereotactic frame system 10. Each laser diode has connected to it an associated electrical power supply cabling.

The preferred laser light sources, useful in accordance with the invention, are helium-neon lasers, although other suitable laser systems known in the art could also be utilized. In particular, other laser systems should be selected depending on what techniques are to be performed, for instance whether the surgeon or health practitioner is to perform diagnostic techniques or surgical techniques. Too, the light sources can be of the same or different colors or wavelengths to provide for ease of use and accuracy.

The invention further comprises a method of determining desired information about a volumetric entity in a body. This method comprises the following steps:

a) positioning a plurality of light beam sources on an apparatus fittable on the body;

b) adjusting the spacing and the rotational positions of the beam sources relative to one another so that the beams emitted therefrom intersect at a point on the volumetric entity of the body; and c) using proportional angulation, determining positional information about the entity.

Steps b) and c) may be repeated a multiplicity of times to a series of points on an area or volume of the volumetric entity to determine positional, area, and volumetric information about the volumetric entity.

The stereotactic computer simulation and graphics techniques which may accompany the use of this invention are not discussed herein, however, computer simulation and graphics techniques, common to the art, and the method and apparatus of co-pending patent application Ser. No. 290,316, are useful in practicing the invention for providing precise measurements, and interactive user-friendly feedback to the health practitioner.

The invention has been described in detail with particular reference to a preferred embodiments thereof, but it will be understood that variations and modifications can be effected within the scope of the invention.

What is claimed is:

1. A stereotactic surgical beam localization apparatus disposed within a surgical microscope, the apparatus comprising:

stereotactic surgical frame means;

objective lens means of said surgical microscope attached to said stereotactic surgical frame means;

beam emitting means comprising laser means disposed within said surgical microscope for emitting at least two beams through said objective lens means from two separate and spaced points;

means for movably adjusting the relative positions to one another of said beam emitting points;

means for aiming said beams at user selected locations on a selected volumetric entity of a body; and means for ascertaining desired information about the selected volumetric entity of the body mathematically from the positions of said beam emitting means in said apparatus, the relative positions to one another of said beam emitting means, and the aiming directions of beams from the beam emitting points.

2. The invention of claim 1 wherein said beam emitting means further comprises prism means disposed within said surgical microscope, wherein said prism means comprise said two separate and spaced points.

3. The invention of claim 1 wherein said beam emitting means are disposed in a spherical relationship to one another.

4. The invention of claim 1 wherein said beam emitting means further comprises laser diode means.

5. The invention of claim 1 wherein said beam emitting means further comprises single laser and fiber optic means.

6. The invention of claim 1 wherein said means for ascertaining desired information comprises means for proportionally angulating the positions and the beam aiming directions of said beam emitting means at a selected point to determine positional information about the selected point.

7. The invention of claim 1 wherein said means for ascertaining desired information comprises means for repeatedly proportionally angulating the position and the beam aiming direction of said beam emitting means at a series of selected points about an area to be measured of the volumetric entity to determine positional and area information about the area to be measured.

* * * * *